(12) United States Patent
Hanagandi et al.

(10) Patent No.: US 6,678,052 B1
(45) Date of Patent: Jan. 13, 2004

(54) ON-LINE SYSTEM FOR MEASURING PROPERTIES OF A PRODUCT

(75) Inventors: Vijay Kumar Millikarjun Hanagandi, Evansville, IN (US); Mark Erik Nelson, Mt. Vernon, IN (US); Ravi Rajamani, West Hartford, CT (US)

(73) Assignee: General Electric Company, Niskayuna, NY (US)

( * ) Notice: Subject to any disclaimer, the term of this patent is extended or adjusted under 35 U.S.C. 154(b) by 433 days.

(21) Appl. No.: 09/677,612

(22) Filed: Oct. 3, 2000

(51) Int. Cl.$^7$ .......................... G01N 21/59; G01N 21/53
(52) U.S. Cl. .................. 356/440; 356/410; 356/436
(58) Field of Search .................. 356/409, 410, 356/411, 246, 440, 436

(56) References Cited

U.S. PATENT DOCUMENTS

| | | | | |
|---|---|---|---|---|
| 3,498,719 A | * | 3/1970 | Wing et al. ................. | 356/442 |
| 3,992,109 A | * | 11/1976 | Bock .......................... | 356/410 |
| 4,172,637 A | * | 10/1979 | Sloane ........................ | 356/319 |
| 5,261,874 A | | 11/1993 | Castle ......................... | 604/4 |
| 5,403,552 A | | 4/1995 | Pardikes ..................... | 422/62 |
| 5,559,173 A | | 9/1996 | Campo et al. .............. | 523/303 |
| 5,568,266 A | * | 10/1996 | Ciza et al. .................. | 356/402 |
| 5,572,320 A | * | 11/1996 | Reintjes et al. ............ | 356/246 |
| 5,644,402 A | * | 7/1997 | Chevallet ................... | 356/440 |

FOREIGN PATENT DOCUMENTS

| | | |
|---|---|---|
| DE | 2133797 A | 1/1973 |
| FR | 2114296 A | 6/1972 |
| FR | 2123948 A | 9/1972 |
| WO | 9729358 A | 8/1997 |

OTHER PUBLICATIONS

Schirmer, RE, "Remote Optic Monitoring Of Polymer Processing Over Long Fiber Optical Cables", ISA Transactions, Instrument Society of America, Pittsburgh, US vol. 28, No. 2, 1989, pp. 65–69, XP000045106. ISSN: 0019–0578 p. 66, para. 2, figure 1.

Foreign Search Report.

* cited by examiner

*Primary Examiner*—Richard A. Rosenberger
(74) *Attorney, Agent, or Firm*—Donald S. Ingraham; Christian G. Cabou

(57) ABSTRACT

An on-line sensor is provided that supplies light to a spectrophotometer to measure the color a product extruded through a conduit having a bypass section. The on-line sensor includes a transparent member with an opaque outer surface and an interior portion extending from a first end to a second end to the transparent member. The interior portion is connected to the bypass section, and the product that flows through the bypass section is supplied to the interior section of the transparent member. A light source connected to the transparent member and provides light to the transparent member inside the opaque outer surface. A light receiver is connected to the transparent member and captures light from the light source in the transparent member that is affected by the product. The captured light is supplied to the spectrophotometer to at least measure the properties of the product supplied to the interior portion of the transparent member.

13 Claims, 7 Drawing Sheets

Figure 1:
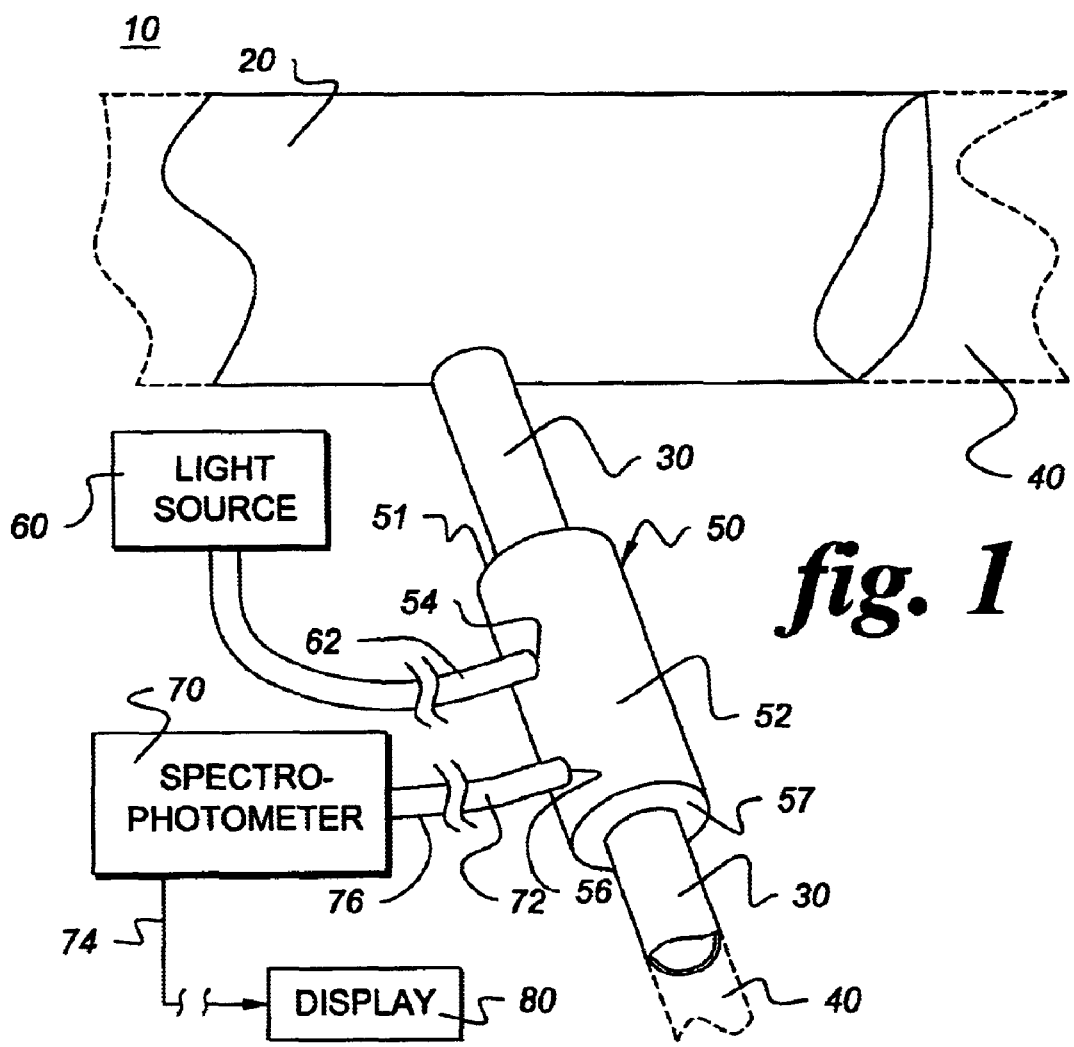

ON-LINE SYSTEM FOR MEASURING PROPERTIES OF A PRODUCT

BACKGROUND OF THE INVENTION

The invention relates to an on-line measurement system for measuring various properties of a product and more particularly to an on-line measurement system for in situ measurement of various properties of a product being flowing through a conduit.

In the manufacturing of some materials, for example, polymeric materials, the product undergoes several manufacturing processes before the final product is created. These processes can be performed in one processing area or at several processing areas. In either case, the product is transported from process to process, or the product is transported to a finishing area. In addition, at the final processing area the product can be formed into various shapes and sizes. Typically, the movement and forming of the product is accomplished by extruding the material through a conduit. Since the conduit is generally chosen for their high strength and low cost and such materials are typically opaque, the conduits are also opaque.

Many processes, especially the finishing process, desire to identify or measure the color and other properties of the product. Color identification and measurement of other properties are desired for, among other things, determining the state of the process, determining the aesthetic value of the product, determining the quality of the product and sorting the product. However, opaque conduits make identification of the color and other properties of the product difficult. In one example, color of the product is identified and measured by directing a portion of the product to a bypass section in the conduit such as a main extruder. A sample of the product is directed through the bypass section where an operator takes a portion of the sampled product. The operator manually supplies the portion of the sampled product to a spectrophotometer where the color is measured. This process of color measurement and identification is time consuming and, therefore, increases the manufacturing time of the product which in turn increase the costs associated with manufacturing.

Therefore, there is a desire for an optical sensor that provides in situ measurement of color and other properties a product as the product flows through a conduit during manufacturing.

BRIEF SUMMARY OF THE INVENTION

In one exemplary embodiment, an on-line sensor is provided that supplies light to a spectrophotometer for in situ measurement of properties of a product while the product is being extruded from conduit that has a bypass section. The on-line sensor includes a transparent member that comprises a first cylindrical section having a first diameter that is connected to the bypass section. A portion of the product flows through the first cylindrical section. A second cylindrical section is also provided that has a second diameter concentric to the first diameter, and the second diameter is greater than the first diameter. The on-line sensor also includes an opaque casing that houses the transparent member and has a first and a second receptacle. A light source is connected to the first receptacle of the opaque casing and provides light to the transparent member inside the opaque casing. A light receiver is connected to the spectrophotometer and the second receptacle of the opaque casing. Also, the light receiver can be positioned at a distant location from the on-line sensor. The light receiver captures light from the light source in the transparent member that is affected by the portion of the product in the first cylindrical section. The captured light is supplied to at least the spectrophotometer for measuring the properties of the portion of product in the first cylindrical section of the transparent member.

BRIEF DESCRIPTION OF THE DRAWINGS

FIG. 1 is a highly simplified perspective and schematic view of one exemplary embodiment of a measurement system;

FIG. 2 is a highly simplified perspective and schematic view of another exemplary embodiment of a measurement system;

FIG. 3 is a perspective view of one exemplary embodiment of a connector in a measurement system;

FIG. 4 is a perspective view of another exemplary embodiment of a connected in a measurement system;

FIG. 5 is a partial cut-away view of one exemplary embodiment of an on-line sensor;

FIG. 6, is a partial cut-away view of another exemplary embodiment of an on-line sensor;

FIG. 7 is a partial cut-away view of even another exemplary embodiment of an on-line sensor;

FIG. 8 is a cut-away view of yet another exemplary embodiment of an on-line sensor;

FIG. 9 is a highly simplified perspective and schematic view of a representative embodiment of a measurement system having a reference channel; and FIG. 10 is a perspective view of a representative embodiment of a measurement system.

DETAILED DESCRIPTION OF THE INVENTION

As shown in FIG. 1, the manufacturing of certain materials, for example, plastics and polymeric materials, into a product 40 involves a conduit 20 through which the product 40 flows. In one embodiment, the extrusion of the product 40 is done to move the product 40 from one location to another. In another embodiment, the extrusion of the product 40 is used to form the product 40 into desired shapes and sizes. Various manufacturing processes desire to use the color and other properties of the product 40 to assist in manufacturing, fabricating and/or sorting. Further, the product specification requires sophisticated color measurements that are more complex than visual measurements and/or determinations of the color. Typically, the conduit 20 is composed of a material that is durable, rigid and inexpensive. Based on these desired properties, the conduit 20 is typically composed of a metallic material that is opaque. Therefore, the color and other properties of the product 40 is determined by a measurement system 10 that views a portion of the product 40 or product 40 that is flowing through the conduit 20.

In FIG. 1, a bypass section 30 is connected to the conduit 20 of the measurement system 10. It should be appreciated that the bypass section 30 can be an existing bypass portion of the conduit 20, and, therefore, a separate by-pass portion is not required but may be used. An on-line sensor 50 is connected to the bypass section 30 via a first end 51 and a second end 57. A portion of the product 40 flows through the bypass section 30 and through the on-line sensor 50 from the first end 51 to the second end 57. The on-line sensor 50 includes an outer surface 52 over its entire surface area including the first end 51 and the second end 57. A first receptacle 54 and a second receptacle 56 are provided on the outer surface 52 of the on-line sensor 50. The first receptacle 54 is connected to a light source 60 via fiber optic bundle 62. The second receptacle 56 comprises a light receiver 72 that is connected via fiber optic bundle 76 to a spectrophotometer 70. A display 80 is connected to the spectrophotometer 70 via connection 74.

In FIG. 1, the measurement system 10 includes an on-line sensor 50 that is connected to the bypass section 30 of the conduit 20. In a representative embodiment, the conduit 20 comprises a viscometer extruder that extrudes the product 40. As disclosed above, a portion of the product 40 that flow through the conduit 20 is directed to flow through the bypass section 30. In another embodiment, the conduit 20 and/or the bypass section 30 include a valve or other mechanism (not shown) that is activated to select when the portion of the product 40 flows through the bypass section 30. In one embodiment to assist in the measurement of the color and other properties of the product 40, the outer surface 52 of the on-line sensor 50 is opaque. In one embodiment, the outer surface 52 comprises an opaque coating, such as, for example, a deposited coating and/or a painted coating. In another embodiment, the outer surface comprises an opaque casing, such as, for example, a metal or plastic housing.

Figure 3:
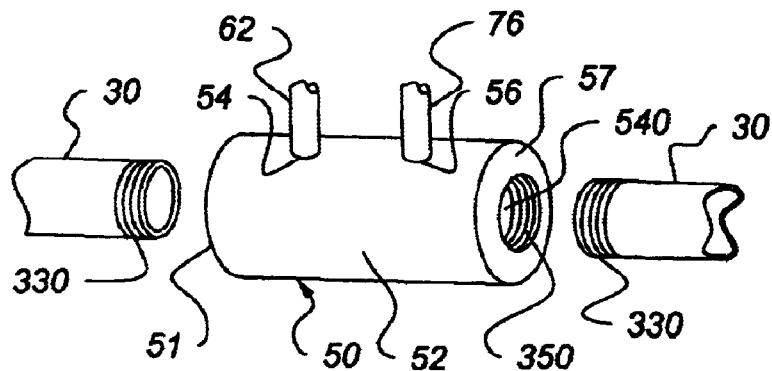

As shown in FIG. 1, the on-line sensor 50 includes a first end 51 and a second end 52. The first end 51 and the second end 57 are connected to the bypass section 30. In one embodiment, as shown in FIG. 3, the first end 51 and the second end 57 are threadily connected to the bypass section 30. In this embodiment, the first end 51 and the second end 57 contain a sensor threaded connector 350 and the bypass section 30 contains bypass threaded connector 330. The sensor threaded connector 350 connects the bypass section 30 via the bypass threaded connector 330 to the interior portion 540 of the on-line sensor 50. In this embodiment, the bypass threaded connector 330 threadily engages the sensor threaded connection 350. It should be appreciated that a sensor threaded connector 350 is located on both the first end 51 and the second end 57. It should also be appreciated that, although the sensor threaded connector 350 is shown as a female connector and the bypass threaded connector 330 is shown as a male connector, the type of connection may be reversed or may comprise a combination of connector types.

Figure 4:
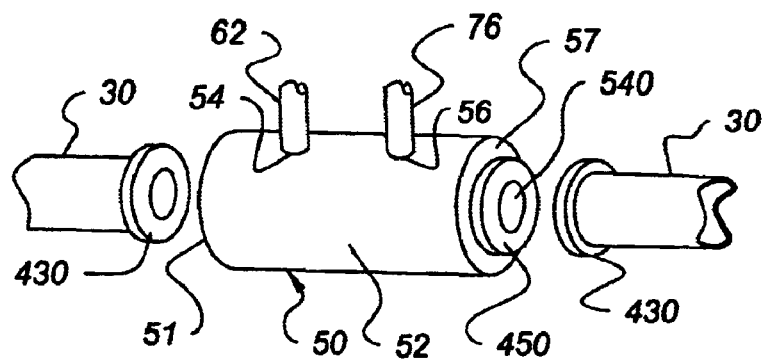

In another embodiment, as shown in FIG. 4, the on-line sensor 50 includes a sensor flange connector 450 that is connected to each of the first end 51 and the second end 57. The sensor flange connector 450 connects to a bypass flange connector 430 on the bypass section 30. The sensor flange connector 450 connects the bypass flange connector 430 to the interior portion 540 of the on-line sensor 50. The sensor flange connector 450 and the bypass flange connector 430 are connected by a coupling device (not shown) such as, for example, bolts and/or screws. It should be appreciated that a sensor flange connector 450 is located on both the first end 51 and the second end 57 of the on-line sensor 50. It should also be appreciated that the on-line sensor 50 can be connected via a variety of other coupling devices and the present invention should not be limited to only those disclosed herein As shown in FIG. 1, the on-line sensor 50 includes a first receptacle 54 and a second receptacle 56. The first receptacle 54 and the second receptacle 56 are located through the outer surface 52 and into the on-line sensor 50 and connect to a light source 60 and a light receiver 72, respectively. The first receptacle 56 is connected to the light source 60 via a fiber optic bundle 62 that comprises, in one embodiment, a plurality of optical fibers housed in an opaque casing. In one embodiment, the light source 60 comprises a calibrated light source 60 such that the light that is supplied to the on-line sensor 50 is precisely controlled. In another embodiment, the light source 60 comprises a white light source. The light receiver 72 can, in one embodiment, comprise the fiber optic bundle 76 that is connected to the spectrophotometer 70. In addition in one embodiment, the fiber optic bundle 76 comprises a plurality of optical fibers. It should be appreciated that the light receiver 72 can comprise any mechanism that collects and/or transmits the light from the on-line sensor 50 to at least the spectrophotometer 70. It should also be appreciated that the fiber optic bundles 62 and 76 can comprise a device that transmits or conducts light from one source to another, and the fiber optic bundles 62 and 76 should not be limited to only those disclosed herein.

The spectrophotometer 70 includes electronics that are used to determine the color and other properties of the product 40 from the light that is received by the light receiver 72. In one embodiment, the color and other properties are measured as the intensity of reflected and/or transmitted light at various wavelengths that may or may not include the visible spectrum. The spectrophotometer 70 is connected to a display 80 via connection 74. In one embodiment, the display 80 provides information and/or data relating to the color or other properties of the product 40. This information can be used by an operator or a control device (not shown) to control the manufacturing process of the product 40. It should be appreciated that the spectrophotometer 70 can be connected to a control device (not shown) such as a microprocessor and supplies control signals or data relating to the color or other properties of the product 40 for controlling the manufacturing of the product 40. In addition, the spectrophotometer 70 may be housed in or connected to a computing device (not shown) that manipulates the light, data and/or information supplied the on-line sensor 50. It should be appreciated that in other embodiments the light receiver 72 can be connected to other analysis devices (not shown) to analyze various properties of the product 40, such as, for example, color of the product 40.

As discussed above, the light receiver 72 can be connected to analysis devices (not shown) in addition to the spectrophotometer 70 to analyze the color and other properties of the product 40. In this regard, the light source 60 can produce light at different wavelengths, such as, for example, light in the infrared, ultraviolet (UV) and visible spectrums. Furthermore, the light is produced at the predetermined wavelength such that the various properties of the product 40 can be measured. The various properties of the product 40 can include, for example, color, additives and other material properties. These various properties can be measured by performing chemimetric analysis on the light that is affected by the product 40. Chemimetric analysis is a statistical analysis determining the absorbance and/or transmission of light that has been affected by the product 40. In one embodiment, the chemimetric analysis of the light affected by the product 40 can detect subtle or minute changes in the light spectra and attribute these changes to compounds, such as, for example, pigments that yield the desired color, that are present in the product 40. In another embodiment, chemimetric analysis can determine if other additives, such as, for example, release and UV stabilizers have been formulated in the product 40. In addition, the chemimetric analysis can determine the condition of the light in the on-line sensor 50 to determine if the optical path has become obscured.

As discussed above, the light supplied to the on-line sensor 50 is used to measure the color and other properties of the product 40. In one embodiment, the product 40 is opaque and has very low light transmission property. As such, these opaque material properties of the product 40 allow very little or even no light to pass through the product 40. Therefore, the portion of the product 40 that is in the on-line sensor 50 reflects light from the light source 60. For this material type, the first receptacle 54 and the second receptacle 56 are positioned on the same side of the on-line sensor 50, as shown in FIG. 1. Thus, the light receiver 72 collects light supplied by the light source 60 that is reflected by the product 40, and the light receiver 72 supplies this light to at least the spectrophotometer 70.

Figure 2:
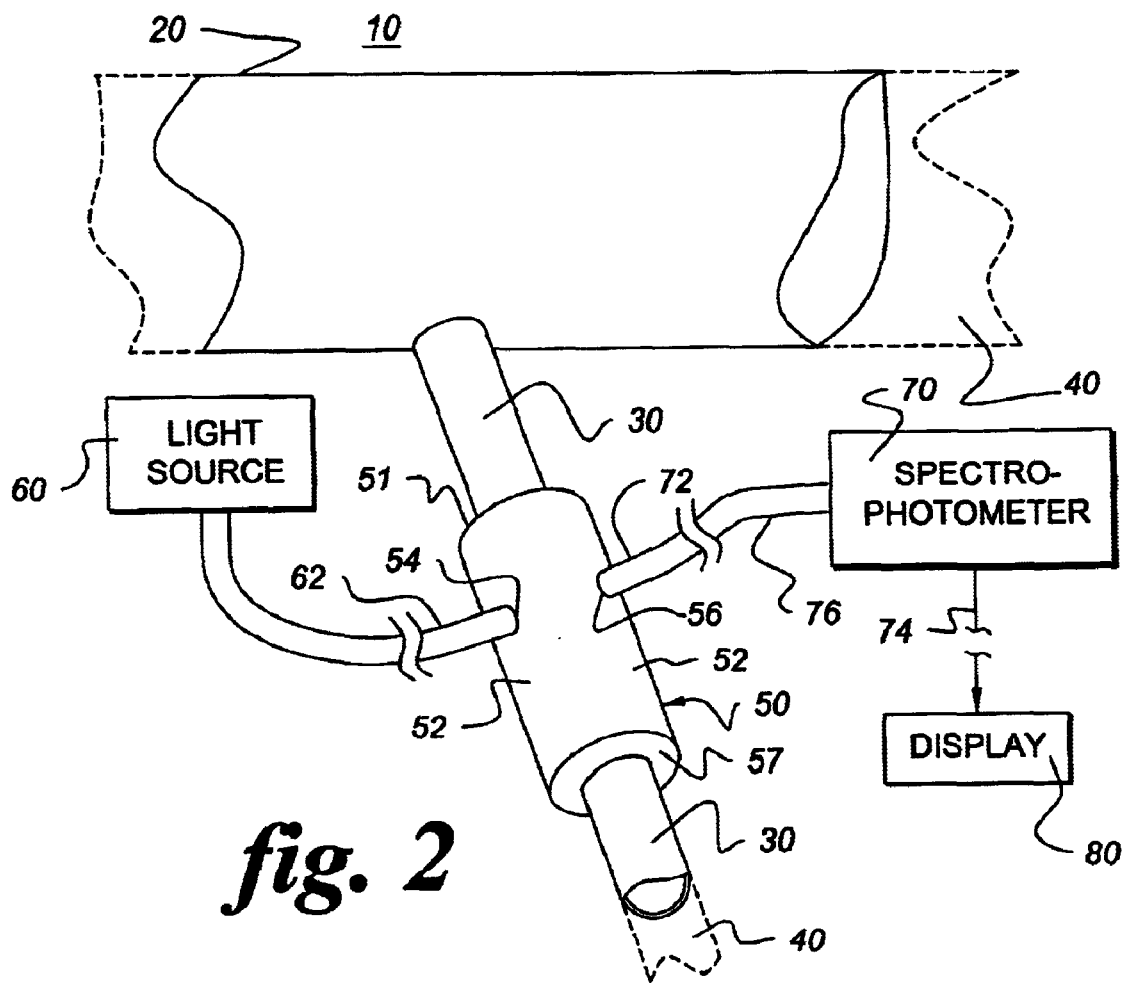

Other products 40 have transparent and/or translucent material properties that allow light to pass through the product 40. To determine the color and other properties of these translucent/transparent materials, the on-line sensor 50 includes, in one embodiment, the first receptacle 54 positioned at about 180 degrees opposite from the second receptacle 56 as shown in FIG. 2. In this embodiment, the light source 60 supplies light to the first receptacle 54 that is transmitted through the product 40, and the transmitted light is collected by the light receiver 72 that is connected to the second receptacle 56. It should be appreciated that, in this embodiment, the first receptacle 54 and the second receptacle 56 can be positioned at angles other than about 180 degrees to measure the color and other properties of the product 40.

With regard to a product 40 that has transparent and/or translucent material properties, the measurement of the color and other properties is difficult because the product 40 may have little or no color. Therefore, in one embodiment, the measurement of the color and other properties in products 40 that are transparent/translucent is performed by measuring the amplitude of light that is transmitted through the product 40 at different wavelengths that may or may not include the visible spectrum. When the product 40 is transparent/translucent, it is desirable to have light pass through the product at a larger distance or path length between the light source 60 and the light receiver 72. The increased path length increases the sensitivity of the on-line sensor 50 by requiring the light to travel through more of the product 40 in order to determine the color and other properties of the product 40.

Figure 6:
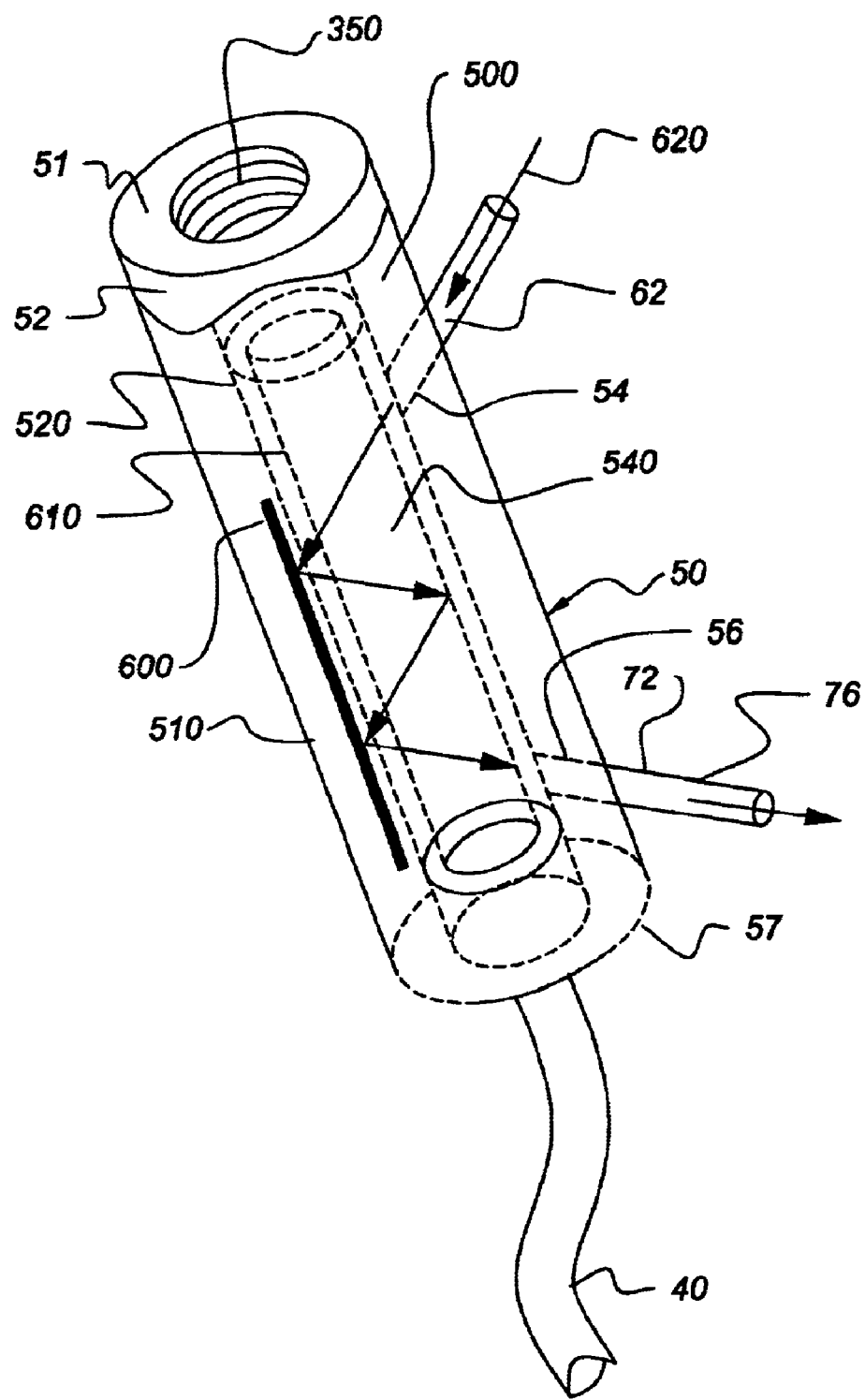

In one embodiment, as shown in FIG. 6, the path length is increased by using a reflective member 600. In this embodiment, the on-line sensor 50 includes a reflective member 600 in the transparent member 500. In a preferred embodiment, the reflective member 600 is positioned near an inside edge 610 of the second cylindrical section 520. In another embodiment, the reflective member 600 is positioned at a location between the first cylindrical section 510 and the second cylindrical section 520. In even another embodiment, the reflective member 600 is positioned outside the transparent member 500 along the first cylindrical section 510. With the reflective member 600, the path length is increased because first receptacle 54 is located at a predetermined distance from the second receptacle 56. The reflective member 600 is positioned between the first receptacle 54 and the second receptacle 56 and is positioned on an opposite side of the second cylindrical section 520 in relation to the first receptacle 54 and the second receptacle 56. The light 620 from the light source 60 via the fiber optic bundle 62 in the first receptacle 54 is directed into the on-line sensor 50. The light 620 passes through the product 40 in the interior portion 540 and is reflected by the reflective member 600. The light 620 then passes through the product 40 in the interior portion 540 a number of times by reflecting off the reflective member 600, and in one embodiment, also reflecting off the second receptacle 56. It should be appreciated that, in this embodiment, that the light 620 is allowed to pass through the product 40 in the interior portion 540 a number of times (as opposed to just one time) before the transmitted light is collected by the light receiver 72 via the fiber optic bundle 76 in the second receptacle 56. In FIG. 6, the reflective member 610 is shown on only one side of the second cylindrical section 520, but in other embodiments, the reflective member 610 is disposed around the entire circumference of a predetermined portion of the second cylindrical section 520. In a preferred embodiment as shown in FIG. 6, the first receptacle 54 and the second receptacle 56 are positioned at an angle other than 90 degrees relative to the transparent member 500. This angular positioning of the first receptacle 54 and the second receptacle 56 is advantageous when introducing light 620 into the interior portion 540 and for collecting the transmitted light 620 because the light 620 is introduced at an angle into the interior portion 540 to increase the path length. However, it should be appreciated that the first receptacle 54 and the second receptacle 56 can be placed at any angle relative to the transparent member 500 including a 90 degree relationship.

Figure 7:
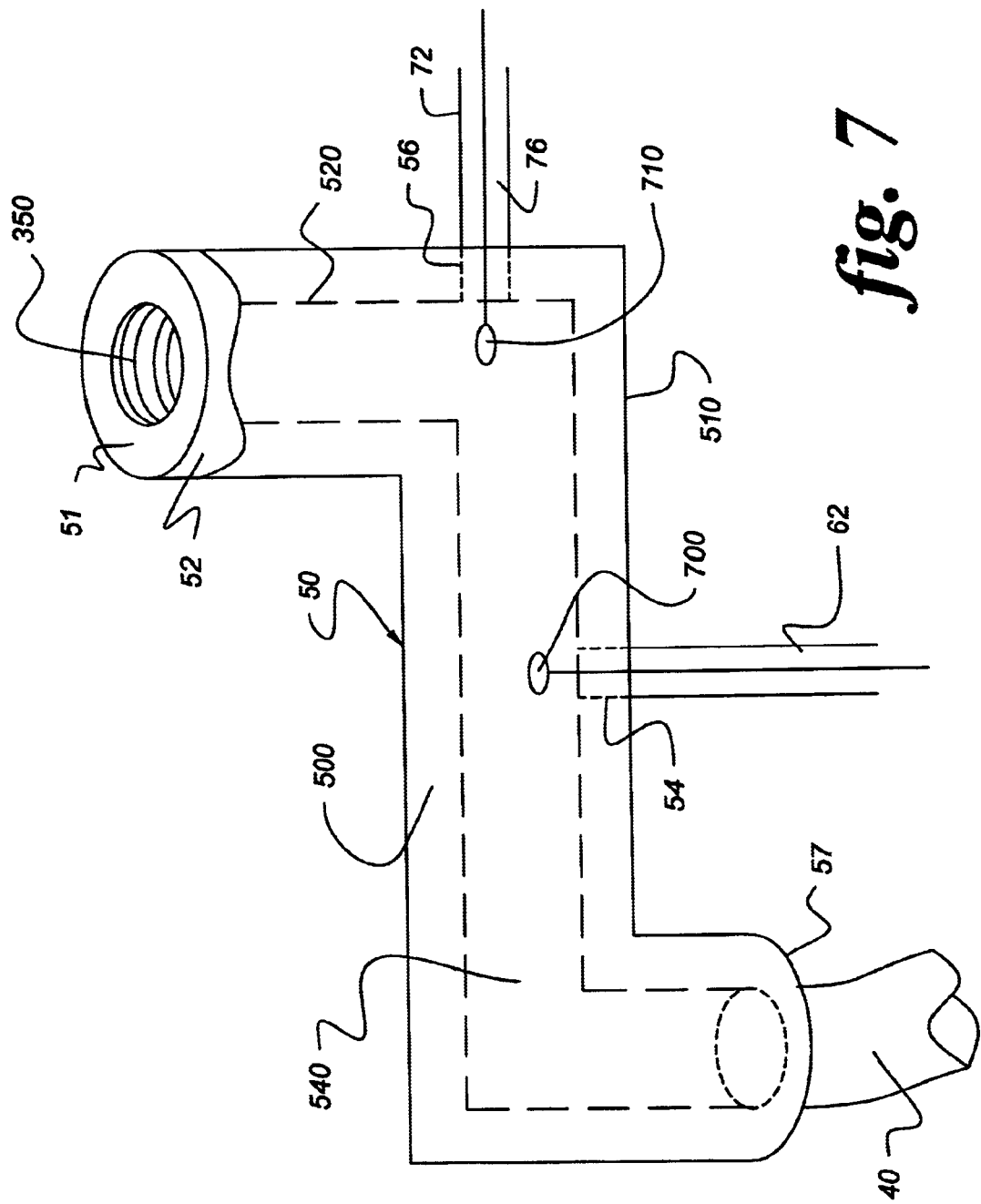

Another embodiment of the on-line sensor 50, as shown in FIG. 7, is used to increase the path length of the light transmitted through the product 40. In this embodiment, the first end 51 and the second end 57 are disposed along different axes. In the embodiment shown in FIG. 7, the on-line sensor 50 includes an interior portion 540 that turns at right angles. However, it should be appreciated that other embodiments include an interior portion 540 that turns at angles other than 90 degrees and interior portions 540 that are substantially linear from the first end 51 to the second end 57. In FIG. 7, a fixed probe 700 is positioned in the transparent member 500 at a location between the first cylindrical section 510 and the second cylindrical section 520. The fixed probe 700 is located in the first receptacle 54 and in one embodiment is part of the fiber optic bundle 62. The fixed probe 700 allows the light source 60 to be place at a specified fixed position in the on-line sensor 50. A variable-position probe 710 is also located between the first cylindrical section 510 and the second cylindrical section 520. The variable-position probe 710 is located in the second receptacle 56 and, in one embodiment, is part of the fiber optic bundle 76 of light receiver 72. The variable-position probe 710 allows the light receiver 72 to be positioned at various points adjacent to the interior portion 540 to increase or decrease the path length of the light transmitted through the product 40 in the interior portion 540. The variable-position probe 710 can be moved to various positions along an axis that is horizontally located between the fixed probe 700 and the variable-position probe 710. This positioning of the variable-position probe 710 can increase or decrease the path length that the light must travel through the product 40 before being collected by the light receiver 72. It should be appreciated that, in one embodiment shown in FIG. 7, the fixed probe 700 comprises the light source 60 while the variable-position probe 710 comprises the light receiver 72. In other embodiments, these positions can be reversed having the light source 72 being associated with the variable-position probe 710 and the light receiver 72 being associated with the fixed probe 700. It should be appreciated that the fixed probe 700 and the variable-position probe 710 can be positioned on the same or opposite side of the transparent member 500. It should also be appreciated that the light from the light source 60 may be affected by the product 40 in other ways other than reflection of and transmission through the product 40, and the present invention should not be limited to the embodiments disclosed herein.

Figure 5:
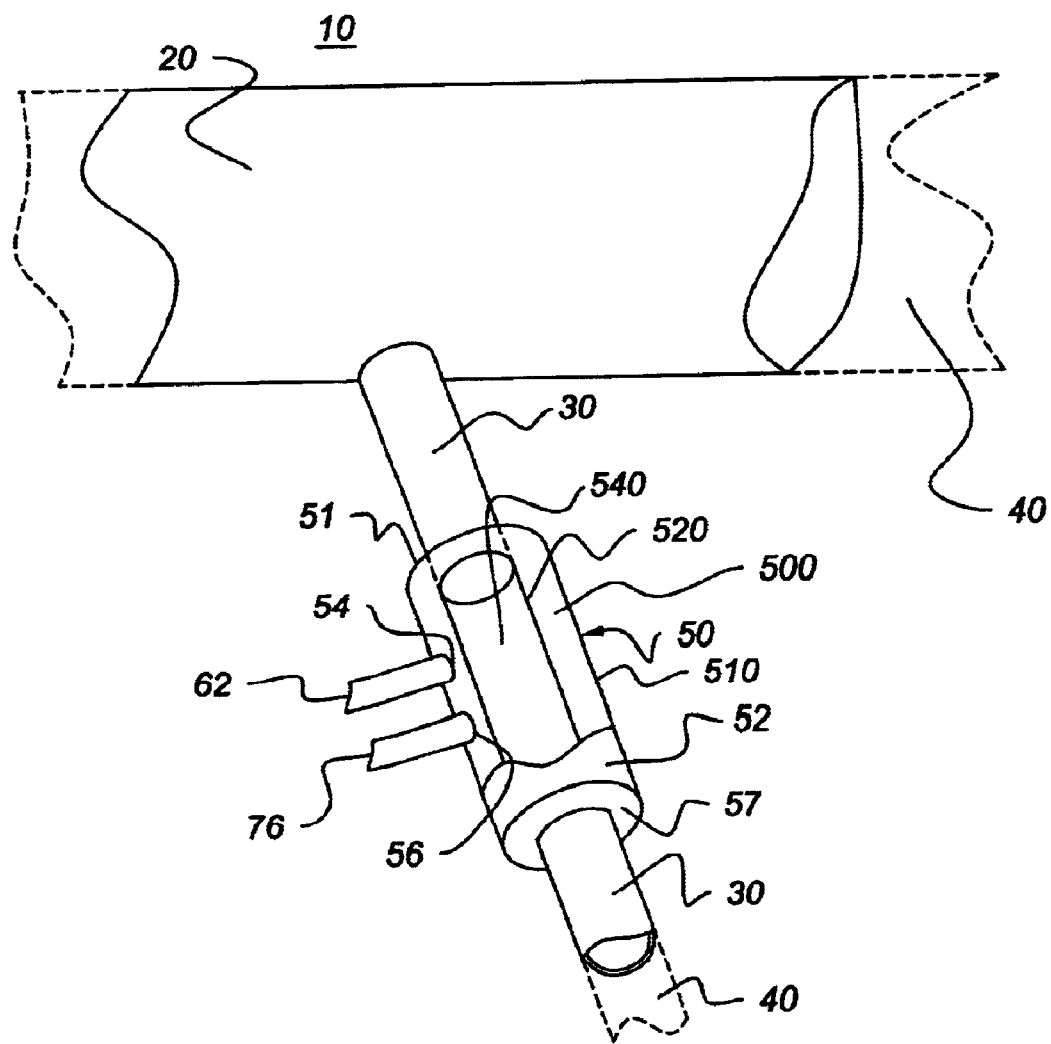

As shown in FIG. 5, the on-line sensor 50 comprises a transparent member 500 having a first cylindrical section 510 that is co-axial with a second cylindrical section 520. The outer surface 52 and an outer edge of an interior portion 540 define the extremities of the first cylindrical section 510. The second cylindrical section 520 defines the interior portion 540 that extends the length of the on-line sensor 50 that is connected to the bypass section 30 via the first end 51 and the second end 57. The portion of product 40 that flows through the bypass section 30 also flows through the interior section 540 of the on-line sensor 50. The transparent member 500 is transparent to allow the light supplied from the light source 60 to be transmitted through the transparent member 500 to the product 40. In a representative embodiment, the transparent member 500 comprises quartz. In another representative embodiment, the transparent member 500 comprises sapphire. The outer surface 52 is provided to ensure that the light supplied to the on-line sensor 50 remains in the on-line sensor 50 and is not dissipated. In this manner, light source 60 that is calibrated can allow the determination of amount of light this is supplied to the on-line sensor 50 by the light source 60 and the amount of light that is collected by the light receiver 72. This information provides valuable insight to the color and/or other properties of the product 40.

Figure 9:
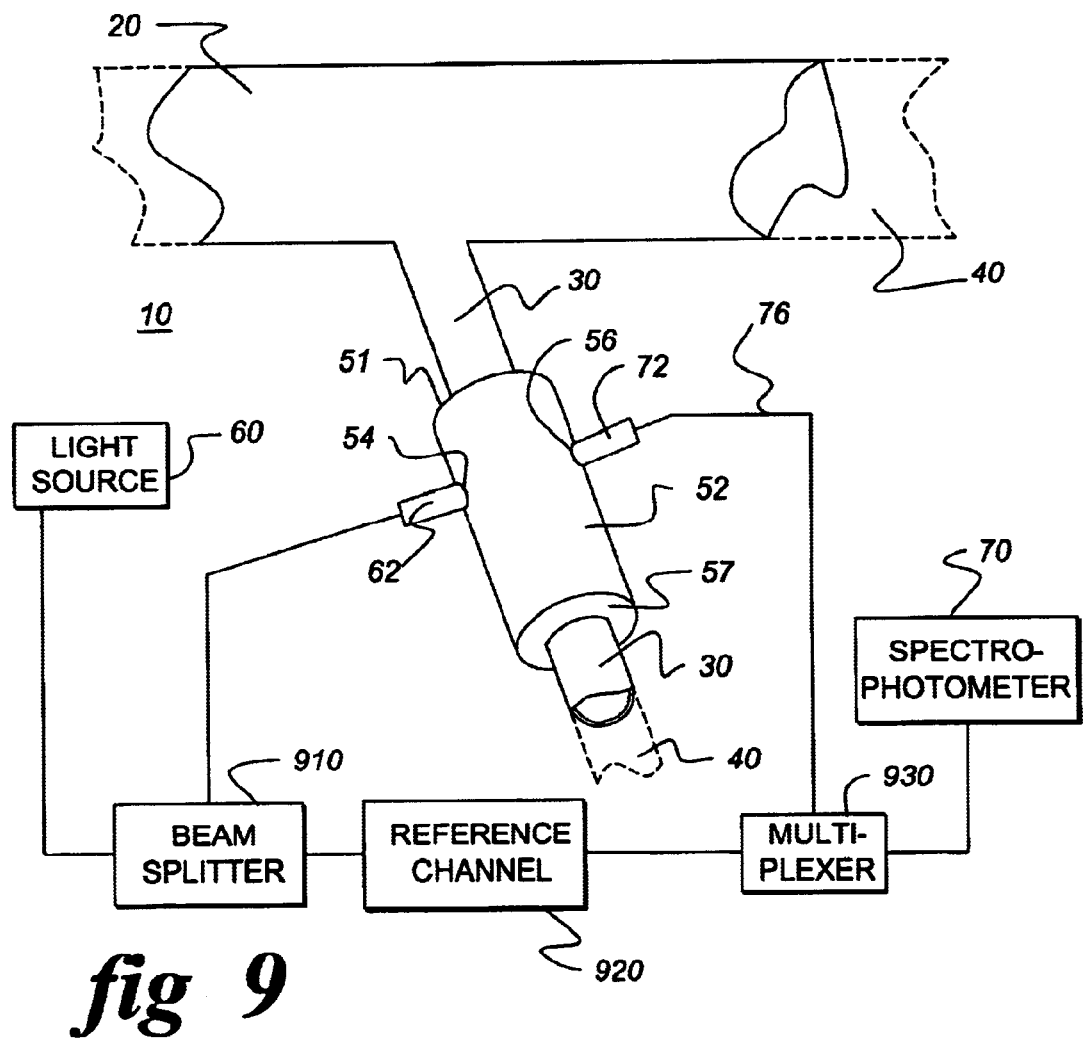

In FIG. 9, another embodiment of the measurement system 10 includes a reference channel 920 that is used to determine a baseline reference point for the light source 60. The reference channel 920 increases the sensitivity of the on-line sensor 50. In this embodiment, a beam splitter 910 splits the light from the light source 60 to both the on-line sensor 50 and the reference channel 920. The light from the reference channel 920 and the light from the light receiver 72 are supplied to an multiplexer 930 that can selectively supply either the light from the reference channel 920 and the light from light receiver 72 to the spectrophotometer 70. In this manner, the multiplexer 930 allows the spectrophotometer 70 to measure both the light from the reference channel 920 and the light from the light receiver 72. As such, the light from the light receiver 72 can be continually or randomly compared to the light from the reference channel 920 to detect any changes caused by variation in the light source 60 and/or degradation in the fiber optic bundles 62 and 76. In addition, if no degradation of the optical path of the reference channel 920 is present, any change in the ratio of the intensity of the light from the light receiver 72 and the light from the reference channel 920 can be compared. The comparison of the light can be used to determine the condition of the optical path in the on-line sensor 50, such as, for example, if the optical path is blocked. It should be appreciated that other analysis devices (not shown) can be connected to the multiplexer 930 to determine the properties of the product 40 and to evaluate the light from the reference channel 920. In even another embodiment, the measurement system 10 can provide a reference of the light from the light source 60. In this embodiment, a statistically constant area of the light spectrum obtained from the light that is affected by the product 40 is analyzed using chemimetric analysis by the spectrophotometer 70 or other analysis devices (not shown). The chemimetric analysis first determines a baseline measurement of the area of the light spectrum and, then, compares later measurement of the light affected by the product 40 to the baseline measurement. As stated above, this reference measurement can determine, for example, degradation in the light source 60 and/or the fiber optic bundles 62 and 76, and the condition of the optical path in the on-line sensor 50 can be determined.

Figure 8:
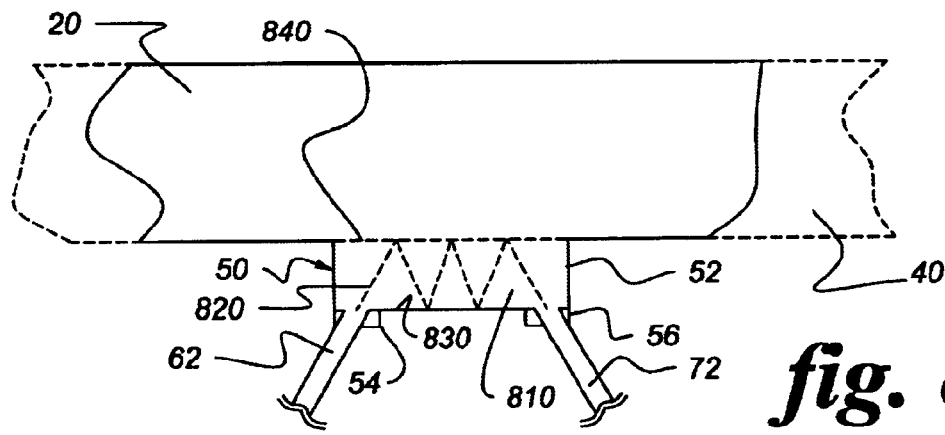

In even another embodiment, as shown in FIG. 8, the on-line sensor 50 comprises a transparent member 810 that is positioned adjacent to an opening 840 in the conduit 20. It should be appreciated that the opening 840 can be included in the by-pass section 30 (FIG. 1) that is connected to the conduit 20. It should also be appreciated that the adjacent positioning of the transparent member 810 to the opening 840 includes, for example, positioning in the opening 840, positioning near the opening 840 and positioning at the opening 840 that seals the opening 840 such that product 40 is prevented from flowing from the opening 840. The transparent member 810 includes an outer surface 52 over the entire area of the transparent member 810 that is not positioned adjacent to the opening 840 in the conduit 20. In one embodiment to assist in the measurement of the color and other properties of the product 40, the outer surface 52 of the on-line sensor 50 is opaque. In one embodiment, the outer surface 52 comprises an opaque coating, such as, for example, a deposited coating and/or a painted coating. In another embodiment, the outer surface comprises an opaque casing, such as, for example, a metal or plastic housing.

The transparent member 810 of the on-line sensor 800 includes a first receptacle 54 and a second receptacle 56 that receive the first fiber optic bundle 62 and the second fiber optic bundle 76, respectively. The first fiber optic bundle 62 can be connected to, for example, a light source 60 (FIG. 1). The second fiber optic bundle 76 can be connected to, for example, a spectrophotometer 70 (FIG. 1) or other analysis devices (not shown). In one representative embodiment, the transparent member 810 comprises sapphire. In another representative embodiment, the transparent member 810 comprises quartz.

In FIG. 8, the on-line sensor 50 can be used to perform an attenuated total reflectance (ATR) technique that increases the sensitivity of the on-line sensor 50 by increasing the path length that the light 820 travels, similar to FIG. 6. In FIG. 8, the on-line sensor 50 is positioned on one side of the conduit 20. The light 820 enters the transparent member 810 via fiber optic bundle 62 and is reflected by the product 400 to the light receiver 72. In this embodiment, the light 820 is reflected by the product 40 and within the transparent member 810 until the light 820 is received by the light receiver 72. In another embodiment, the transparent member 810 includes a reflective surface 830 inside the outer coating 52 to facilitate the reflectance of the light 820 in the transparent member 810. In addition, it should be appreciated that the on-line sensor 50, in FIG. 8, can be used to measure the color and other properties of the product 40 that have, for example, transparent, semi-transparent or opaque properties. It should also be appreciated that in the on-line sensor 50 of FIG. 8 the alignment of the fiber optic bundle 62 and the light receiver 72 can tolerate misalignment without sacrificing the sensitivity of the light 820 that is affected by the product 40.

Figure 10:
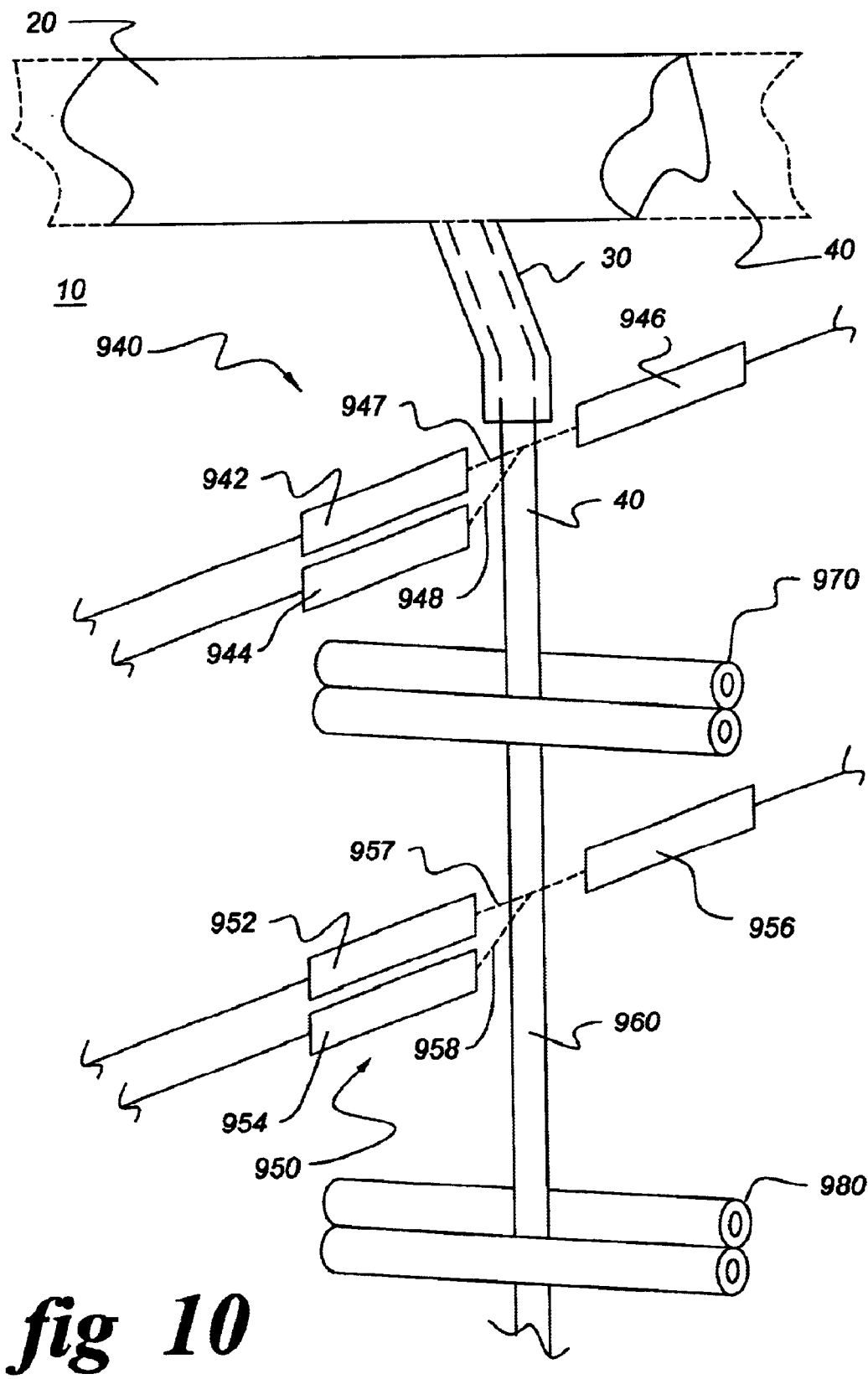

In another representative embodiment, as shown in FIG. 10, an on-line measurement system 10 comprises a conduit 20 having a by-pass section 30 wherein the product 40 flows from the by-pass section 30. The flow of the product 40 from the by-pass section 30 is assisted by drive mechanism 980 that contacts the product 40 and provides a pulling force to assist the product 40 to flow from the by-pass section 30. The drive mechanism 980 can comprise, for example, drive rollers that pull and compress the product 40 and other mechanisms that provide a force that assists the product 40 from the by-pass section 30. It should be appreciated that the product 40, in other embodiments, flows directly from the conduit 20 or a hole in the conduit 20.

In FIG. 10, as the product 40 flows from the by-pass section 30, a first sensor 940 is positioned adjacent to the product 40 to determine properties of the product 40 from light 947 and 948 affected by the product 40. The first sensor 940 comprises a first light source 942 positioned adjacent to a first side of the product 40. A first light receiver 946 is positioned adjacent to a second side of the product 40 to receiver light 947 that is transmitted by the light source and passes through the product 40. For products 40 that have reflective properties, a first reflective light receiver 944 is positioned adjacent to the first side of the product 40 to receiver light 948 that is reflected by the product 40. The first light receiver 946 and first reflective light receiver 944 are connected to an analysis device (not shown), as such, from example, a spectrophotometer 70 (FIG. 1). As described herein above, the first sensor 940 can include a reference channel (shown in FIG. 9) connected to the first light source 942, the first light receiver 946 and the first reflective light receiver 944 to provide a light reference to the analysis device (not shown).

As shown in FIG. 10, a temperature reduction mechanism 970 is positioned after the first sensor 940 to reduce the temperature of the product 40 to product a cooled product. In one embodiment, the temperature of the product is reduced to ambient temperature. The temperature reduction mechanism 970 can comprise, for example, rollers that contact the product 40, chilled rollers that contact the product 40, an air source that provides an air flow to the product 40, a chemical application that is provided on the product 40 or any other mechanism or technique that lowers the temperature of the product 40. A second sensor 950 is located after the temperature reduction mechanism 970 to determine properties of the cooled product 960 from light 957 and 958 affected by the cooled product 960. The second sensor 950 comprises a second a second light source 952 positioned adjacent to a first side of the cooled product 960. A second light receiver 956 is positioned adjacent to a second side of the cooled product 960 to receiver light 957 from the second light source 952 that is transmitted through the cooled product 960. In addition, a second reflective light receiver 954 is positioned of a first side of the cooled product 960 to receive light 958 that is reflected by the cooled product 960. The second light receiver 956 and the second reflective light receiver 954 are connected to an analysis device (not shown), such as, for example, a spectrophotometer 70 (FIG. 1). The analysis device (not shown) receives light 947 and 948 from the product 40 before cooling and receives light 957 and 958 from the cooled product 960. Therefore, the analysis device (not shown) can individually determine the properties of the product 40 and the cooled product 960 and compare the properties of the product 40 and the cooled product 960. The comparison of the properties of the product 40 and cooled product 960 can provide additional information relating to the production and manufacturing of the product 40, such as, for example, the addition of certain additives in the product 40, the state of the product 40 at various stages of the manufacturing process and the overall quality of the product 40. It should be appreciated that, as described above, the second sensor 940 can include a reference channel (shown in FIG. 9) that is connected to the second light source 952, the second light receiver 946 and the second reflective light receiver 954 to provide a light reference to the analysis device (not shown).

It should also be appreciated that since the first sensor 940 and the second sensor 950 are not enclosed, the reference channels (shown in FIG. 9) can be provided to determine changes in, for example, the light sources 942, changes in the measurement system 10 and changes in the ambient light that can affect the determination of the properties of the product 40 and/or the chilled product 960.

The foregoing discussion of the invention has been presented for purposes of illustration and description. Further, the description is not intended to limit the invention to the form disclosed herein. Consequently, variations and modifications commensurate with the above teachings and with the skill and knowledge of the relevant art, are within the scope of the present invention. The embodiment described herein above is further intended to explain the best mode presently known of practicing the invention and to enable others skilled in the art to utilize the invention as such, or in other embodiments, and with the various modifications required by their particular application or uses of the invention. It is intended that the appended claims be construed to include alternative embodiments to the extent permitted by the prior art.

What is claimed is:

1. An on-line measurement system for determining properties of a product flowing from a conduit, the on-line measurement system comprising:

a light source positioned adjacent to the product flowing from the conduit and providing light having a predetermined wavelength to the product, the product affecting the light;

a light receiver positioned adjacent to the product flowing from the conduit and receiving the light affected by the product;

an analysis device connected to the light receiver and analyzing the light received by the light receiver to determine the properties of the product;

a temperature reduction mechanism positioned after the light source and the light receiver and reducing the temperature of the product flowing from the conduit;

a second light source positioned after the temperature reduction mechanism and adjacent to the cooled product, the second light source providing light having a predetermined wavelength to the cooled product, the cooled product affecting the light; and a second light receiver positioned after the temperature reduction mechanism and adjacent to the cooled product, the second light receiver connected to the analysis device and receiving and supplying the light affected by the cooled product to the analysis device for analysis.

2. The one-line measurement system of claim 1 wherein the light source is positioned on a first side of the product flowing from the conduit and the light receiver is positioned on a second side of the product flowing from the conduit to receive light transmitted through the product.

3. The one-line measurement system of claim 1 wherein the light source and the light receiver are positioned on a first side of the product flowing from the conduit, the light receiver receiving light reflected by the product.

4. The on-line measurement system of claim 1 further comprising a reference channel connected to the light source and the analysis device, the reference channel providing a light reference from the light source to the analysis device.

5. The on-line measurement system of claim 1 further comprising:

a beam splitter connected to the light source and splitting the light from the light source into at least two different light paths including a first light path providing light to the product;

a reference channel connected to the beam splitter and receiving a second path of light from the beam splitter, the reference channel providing a light reference based on the light from the second light path; and a multiplexer connected to the reference channel the light receiver and the analysis device, the multiplexer selectively providing light from the reference channel and the light receiver to the analysis device for analysis.

6. The one-line measurement system of claim 1 wherein the second light source is positioned on a first side of the cooled product and the second light receiver is positioned on a second side of the cooled product to receive light transmitted through the cooled product.

7. The one-line measurement system of claim 1 wherein the second light source and the second light receiver are positioned on a first side of the cooled product, the second light receiver receiving light reflected by the cooled product.

8. The on-line measurement system of claim 1 further comprising a reference channel connected to the second light source and the analysis device, the reference channel providing a light reference from the second light source to the analysis device.

9. The on-line measurement system of claim 1 further comprising:

a beam splitter connected to the second light source and splitting the light from the second light source into at least two different light paths including a first light path providing light to the cooled product;

a reference channel connected to the beam splitter and receiving a second path of light from the beam splitter, the reference channel providing a light reference based on the light from the second light path; and a multiplexer connected to the reference channel, the second light receiver and the analysis device, the multiplexer selectively providing light from the reference channel and the second light receiver to the analysis device for analysis.

10. The on-line measurement system of claim 1 wherein the light source comprises a white light source.

11. The on-line measurement system of claim 1 wherein the light source comprises a calibrated light source.

12. The on-line measurement system of claim 1 wherein the second light source comprises a white light source.

13. The on-line measurement system of claim 1 wherein the second light source comprises a calibrated light source.

* * * * *